US012635872B2

(12) United States Patent
Bor et al.

(10) Patent No.: US 12,635,872 B2
(45) Date of Patent: May 26, 2026

(54) MEASURING REFRACTIVE ERROR OF THE HUMAN EYE USING OPTICAL COHERENCE TOMOGRAPHY

(71) Applicant: Alcon Inc., Fribourg (CH)

(72) Inventors: Zsolt Bor, San Clemente, CA (US); Alireza Malek Tabrizi, Fremont, CA (US)

(73) Assignee: Alcon Inc., Fribourg (CH)

( * ) Notice: Subject to any disclaimer, the term of this patent is extended or adjusted under 35 U.S.C. 154(b) by 327 days.

(21) Appl. No.: 18/463,160

(22) Filed: Sep. 7, 2023

(65) Prior Publication Data

US 2024/0081639 A1     Mar. 14, 2024

Related U.S. Application Data

(60) Provisional application No. 63/406,608, filed on Sep. 14, 2022.

(51) Int. Cl.
| | |
|---|---|
| *A61B 3/14* | (2006.01) |
| *A61B 3/00* | (2006.01) |
| *A61B 3/10* | (2006.01) |
| *A61B 3/103* | (2006.01) |
| *A61B 3/117* | (2006.01) |
| *A61B 3/12* | (2006.01) |

(52) U.S. Cl.
CPC ............ *A61B 3/103* (2013.01); *A61B 3/0025* (2013.01); *A61B 3/102* (2013.01); *A61B 3/1035* (2013.01); *A61B 3/117* (2013.01); *A61B 3/1225* (2013.01); *A61B 2505/05* (2013.01)

(58) Field of Classification Search
CPC ....... A61B 3/103; A61B 3/0025; A61B 3/102; A61B 3/1035; A61B 3/117; A61B 3/1225; A61B 2505/05
USPC ................................................. 351/205, 206
See application file for complete search history.

(56) References Cited

U.S. PATENT DOCUMENTS

| | | | |
|---|---|---|---|
| 2015/0077705 A1 | 3/2015 | Artsyukhovich et al. | |
| 2020/0221946 A1 * | 7/2020 | Mino | A61B 3/18 |
| 2022/0400942 A1 * | 12/2022 | Leung | A61B 3/0025 |

FOREIGN PATENT DOCUMENTS

| | | | | |
|---|---|---|---|---|
| WO | WO-2014111759 A1 * | 7/2014 | | A61B 3/1015 |
| WO | WO-2021134087 A1 * | 7/2021 | | A61B 3/0075 |

* cited by examiner

*Primary Examiner* — Mahidere S Sahle

(57) ABSTRACT

Particular embodiments disclosed herein provide an apparatus for performing optometric measurements includes an optical coherence tomography (OCT) imaging system configured to output scanned parallel laser beams across a patient's eye. A line in the OCT image is identified, the line representing a retina of the patient's eye. A shape of the line is then used by the refractive error calculator to measure refractive error of the patient's eye. The height of the line due to curvature indicates degree of myopia or hyperopia. More complex curvature of the line corresponds to higher order aberrations. OCT images for a plurality of section planes may be used to calculate a wavefront elevation map.

20 Claims, 14 Drawing Sheets

310 um

MEASURING REFRACTIVE ERROR OF THE HUMAN EYE USING OPTICAL COHERENCE TOMOGRAPHY

TECHNICAL FIELD

The present disclosure relates generally to approaches for measuring the refractive error of an eye.

BACKGROUND

An optical coherence tomography (OCT) system directs a coherent light beam at a patient's eye, some of which is scattered back to the OCT system. Interference between the scattered light and a portion of the original coherent light beam is used to measure the position of the location of a point from which the light was scattered. Ophthalmic OCTs are primarily used to measure ocular dimensions and diagnose various ocular pathologies. Ophthalmic OCTs may also be used to image the anterior chamber of the eye.

BRIEF SUMMARY

The present disclosure relates generally to the measurement of refractive error of an eye using OCT.

In this patent application an optical coherence tomography (OCT) imaging system is configured to scan parallel beams across a patient's eye. A computing device is configured to receive an OCT signal reflected from the retina. The apparent shape of the retina, in particular the deviation of the apparent shape of the retina from a straight line is used to calculate the refractive error of the eye. For an eye, free of all optical errors the apparent image of the retina is a straight line.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

The refractive errors of the human eye can be measured with Shack-Hartman, Talbot-Moire, Tracey, or Tscherning wavefront meters. Below a new kind of device is described, which can measure the refractive error and the wavefront error of the human eye. The device is based on Fermat's principle and uses an OCT scanner. Ophthalmic OCT was invented in 1991, however, it has not been used or thought of as being capable of measure measuring the refraction and the wavefront errors of the eye.

An optical coherence tomography (OCT) system directs one beam (called the signal beam) from a laser beam at the eye of a patient and another beam (called the reference beam) from the laser beam into a reference arm. The back-reflected beams from the two arms are then combined. As a result of the combination of the beams, a wavelength dependent interference spectrum is formed. By analyzing the interference spectrum, two pieces of information can be obtained: (a) the intensity of the back-reflected light from the eye and (b) the Z depth location of the origin of the back-reflected light. The Z location can also be expressed either in Z distance or in propagation time of the light $T=Z/c$ where c is the speed of the light. For purposes of the embodiments described herein, the propagation time T is the most relevant parameter. A measurement along one direction of propagation is called an A scan. By scanning the OCT beam in X and Y directions many thousands of A scans can be made. From the plurality of A scans, a 3D image of the eye can be reconstructed. From the 3D image, X/Z or Y/Z side views or an X/Y en face images are typically displayed. Ophthalmic OCTs are primarily used to image the cornea, the anterior chamber, the lens, the vitreous and the retina. The images are used to measure ocular dimensions and diagnose different kind of ocular pathologies.

Figure 1:
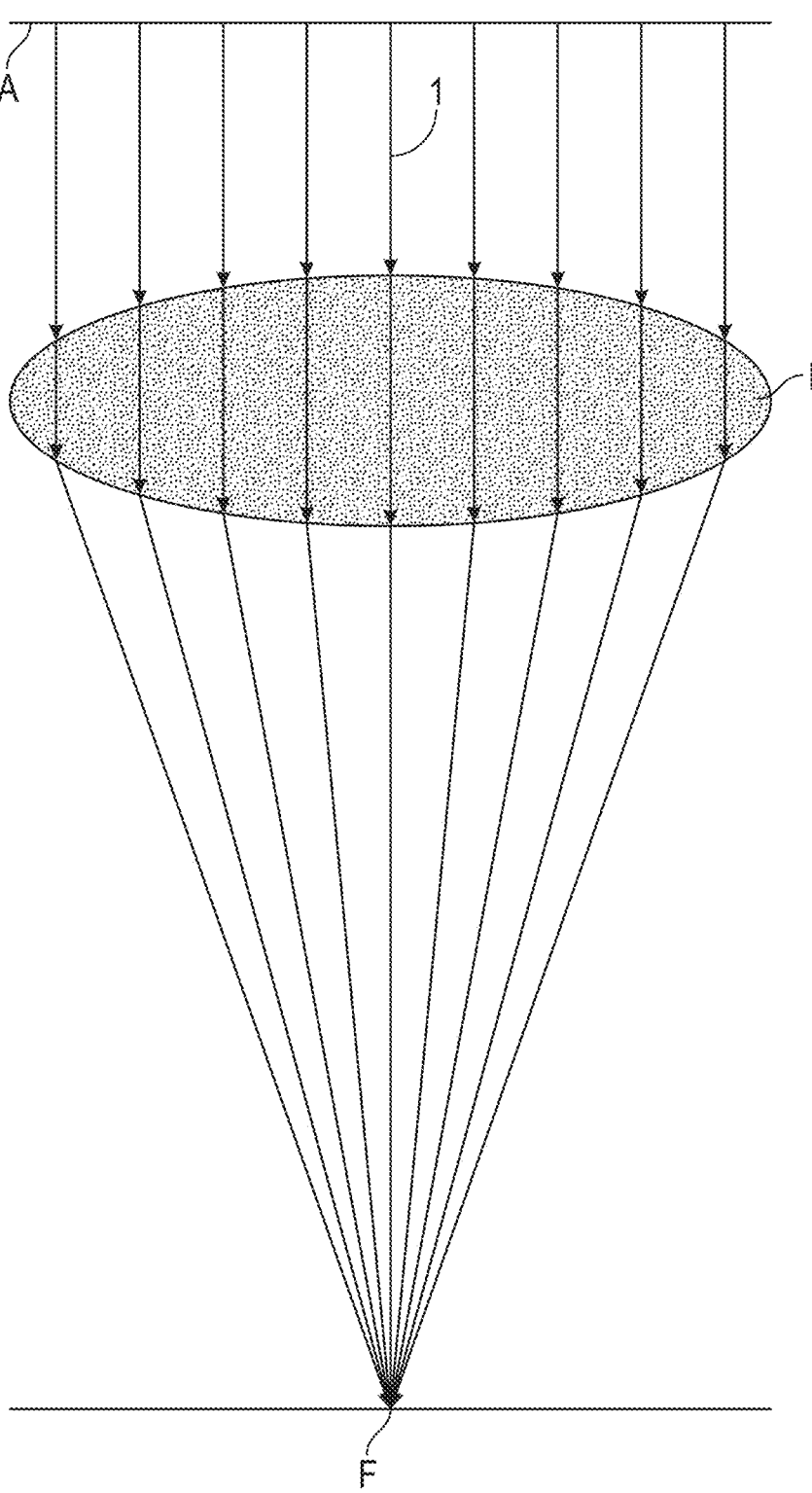
FIG. 1 illustrates a perfect, aberration-free lens illuminated with a plurality of parallel rays such that all rays are focused to the focal point F.

Referring to FIG. 1, to measure the refractive error of the eye using OCT, the more than 350 years old Fermat's principle is used. This principle states that the propagation time of flight from plane A to the focal point F is the same for any of the rays. Fermat's principle can be applied for a perfect lens L which is illuminated with a plane wave propagating parallel to the optical axis of the lens. The geometrical path length from plane A to focal point F is the shortest for ray 1 but this is the ray which travels the longest path in the material of the lens. The propagation time in the lens is slower and corresponds to c/n, where c is the speed of light in vacuum and n is the refractive index of the material of the lens.

Figure 2B:
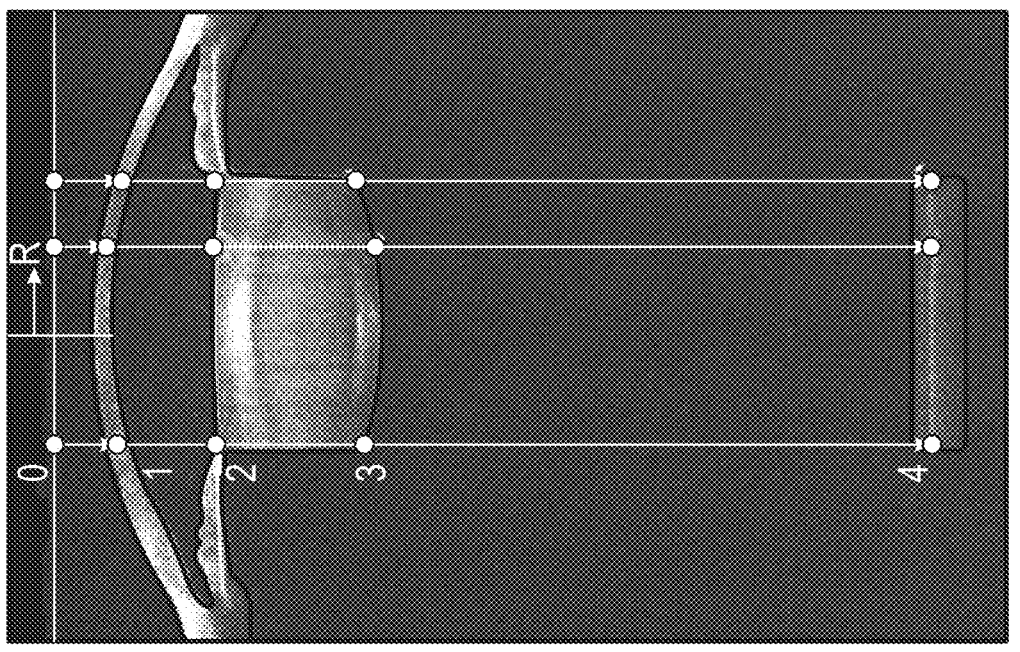
FIG. 2B illustrates an OCT image of an aberration-free eye. eye showing a stretched representation of the focal point in accordance with certain embodiments.
Figure 2A:
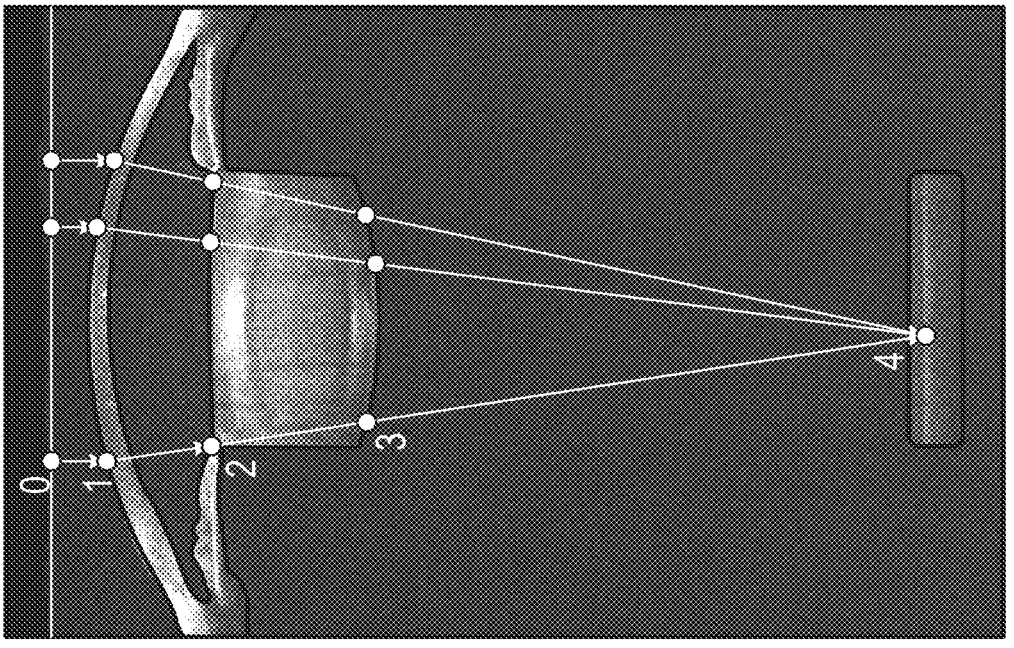
FIG. 2A illustrates an OCT image of an aberration-free eye showing actual ray propagation to a focal point on the retina of the eye.

FIGS. 2A-2B below are used to described how Fermat's principle applies to an OCT image of an eye having zero refractive error. Note that an OCT device displays the propagation time of the rays as a function of the input R location of the OCT rays.

Referring to FIG. 2A, parallel OCT rays are propagated onto the eye. If the eye does not have a refractive error, such that all beams are focused on the retina, the propagation time would be the same for all rays shown in FIG. 2A.

When creating the OCT image, the propagation time is plotted as a function of the R input position of the entry beam. When displaying the OCT image of the eye, the refractions and beam deflections on the curved surfaces of the cornea and the lens are ignored. Since the propagation time is the same for every ray, the retinal focal point appears as a straight line (4), as shown in FIG. 2B. Note that the straight line (4) in FIG. 2B is not the image of the retina but an image of the point (4) in FIG. 2A of the retina that is stretched horizontally. It is important to remember that the horizontal line is not the retinal image; the horizontal line just appears as the image of the retina. In reality, it is the image of a small portion of the retina, which is stretched horizontally. The length of the stretching equals to the scanning length of the OCT beam above the cornea. The latter is often limited by the size of the pupil.

Certain OCT devices partially take into account deflection of the beam caused by the refraction on the oblique surfaces but for the purposes of the embodiments described here such OCT software is used which does not correct for the beam deflection of the curved and oblique surfaces.

Presently there are two existing approaches when it comes to OCT imaging: retinal OCT and anterior chamber OCT. In an anterior chamber OCT, the central, axial beam of the OCT above the cornea is always strictly vertical and scanned along the horizontal direction. The beam waist of the incident OCT beam is in the anterior chamber-lens complex, which helps the OCT to efficiently collect the backscattered light from the anterior chamber. In retinal OCT the beam is focused on the retina level and the axial beams of the OCT beam are not strictly parallel. Instead, the incident beams form a shape of handheld fan the rotation axis of which is located in the pupil of the eye. In this way a very large angular range of the retina can be scanned.

The OCT described in this patent application is similar to the anterior chamber OCT in the sense that the central, axial beams are always strictly vertical and are scanned horizontally but the beam waist is focused onto the retinal level. Such focusing ensures efficient collection of the backscattered light from the retina. Such system will be referred in this patent application as modified anterior chamber OCT. Some variation from strict verticality can be corrected for as described below such that in some implementations, the axial beams are only substantially vertical and parallel to one another, e.g., within 2 degrees of vertical and parallel.

Figure 3:
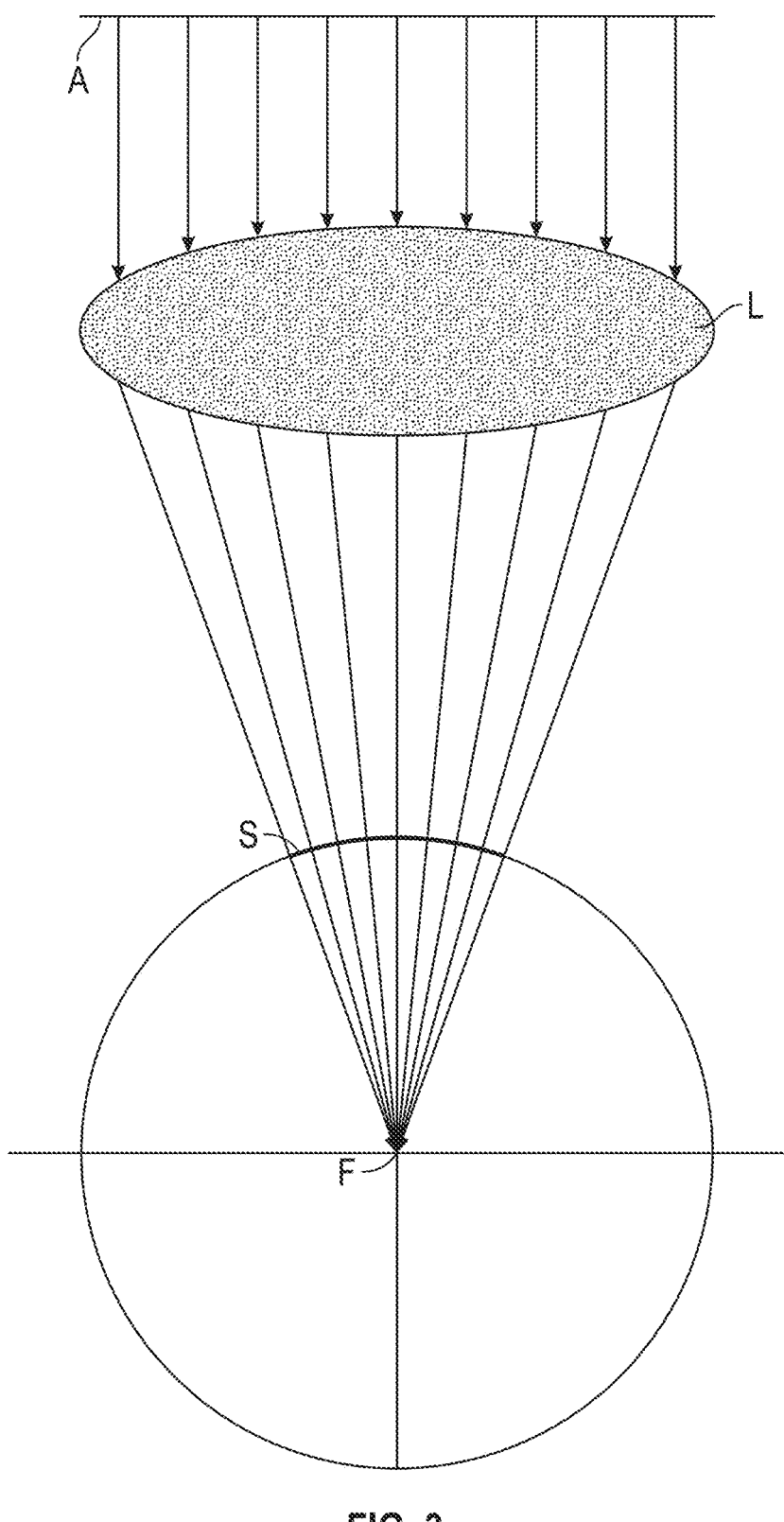
FIG. 3 illustrates Fermat's principle as applied to rays passing through a lens.

Referring to FIG. 3, suppose a circular surface S is centered on the focal point F of the lens L. From Fermat's principle it also follows that the propagation time of the light from plane A to the spherical surface S is equal for any of the rays. S is therefore a surface of equal propagation time.

Figure 4:
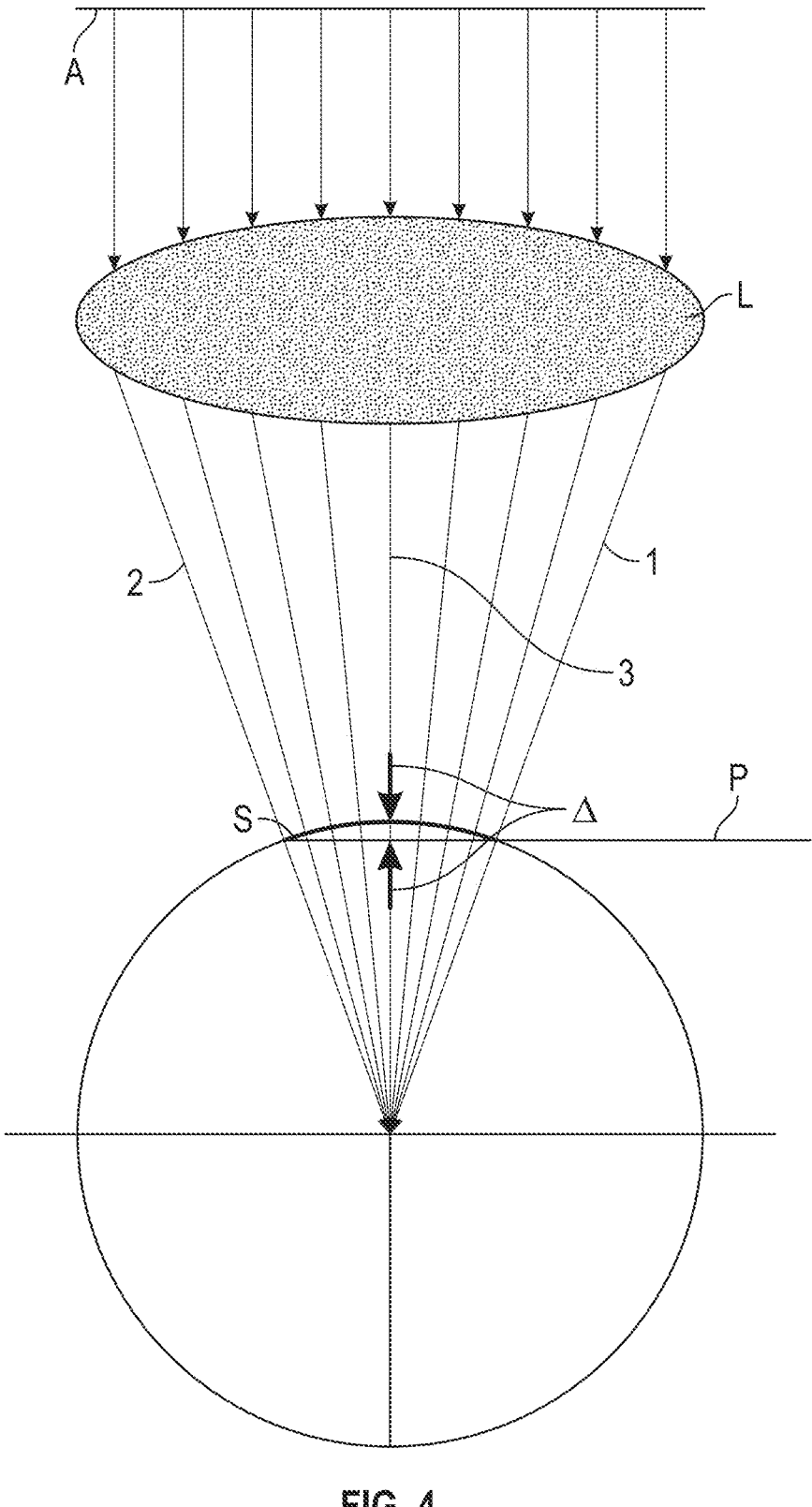
FIG. 4 Illustrates the surface S which is a surface of equal light propagation time from plane A to the surface S.
Figures 5A, 5B:
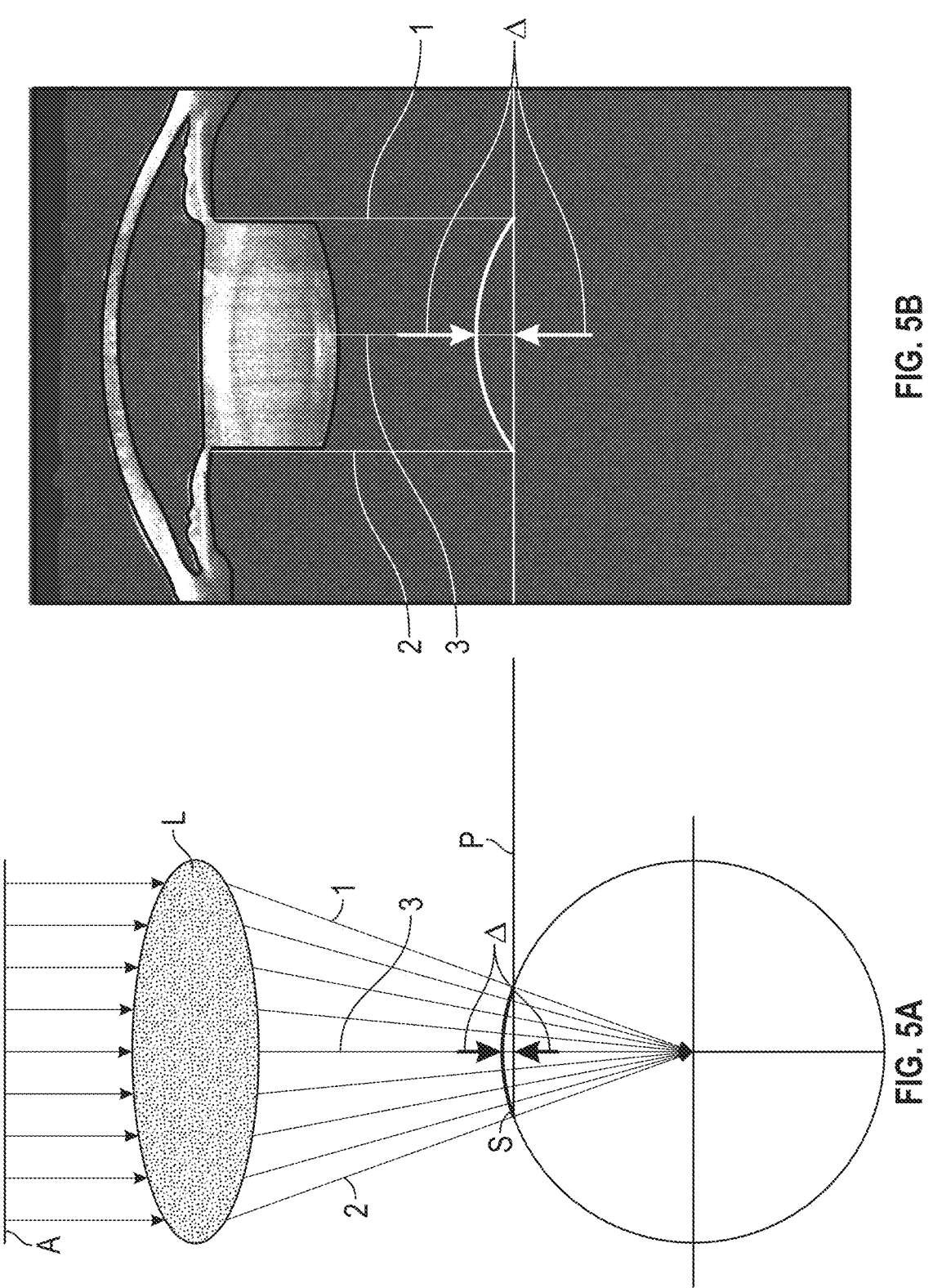
FIGS. 5A and 5B illustrate the OCT image of plane P that is offset upwards from the focal point of a lens in an OCT image, in accordance with certain embodiments.

Referring to FIG. 4, a reflective plain surface P is assumed to be put above the focal point F. As shown in FIG. 4, rays 1 and 2 are the first to arrive onto plane P. Ray 3 is the last ray to arrive onto plane surface P. The arrival time difference Δ is Δ/c where c is the speed of light. The propagation time from plane A to the spherical surface S is equal for any of the rays. Referring to FIGS. 5A and 5B, the appearance of the surface P on the refractive error measuring OCT image is as a curved line having a sag Δ measured along the optical axis of the lens L.

Figures 6A, 6B:
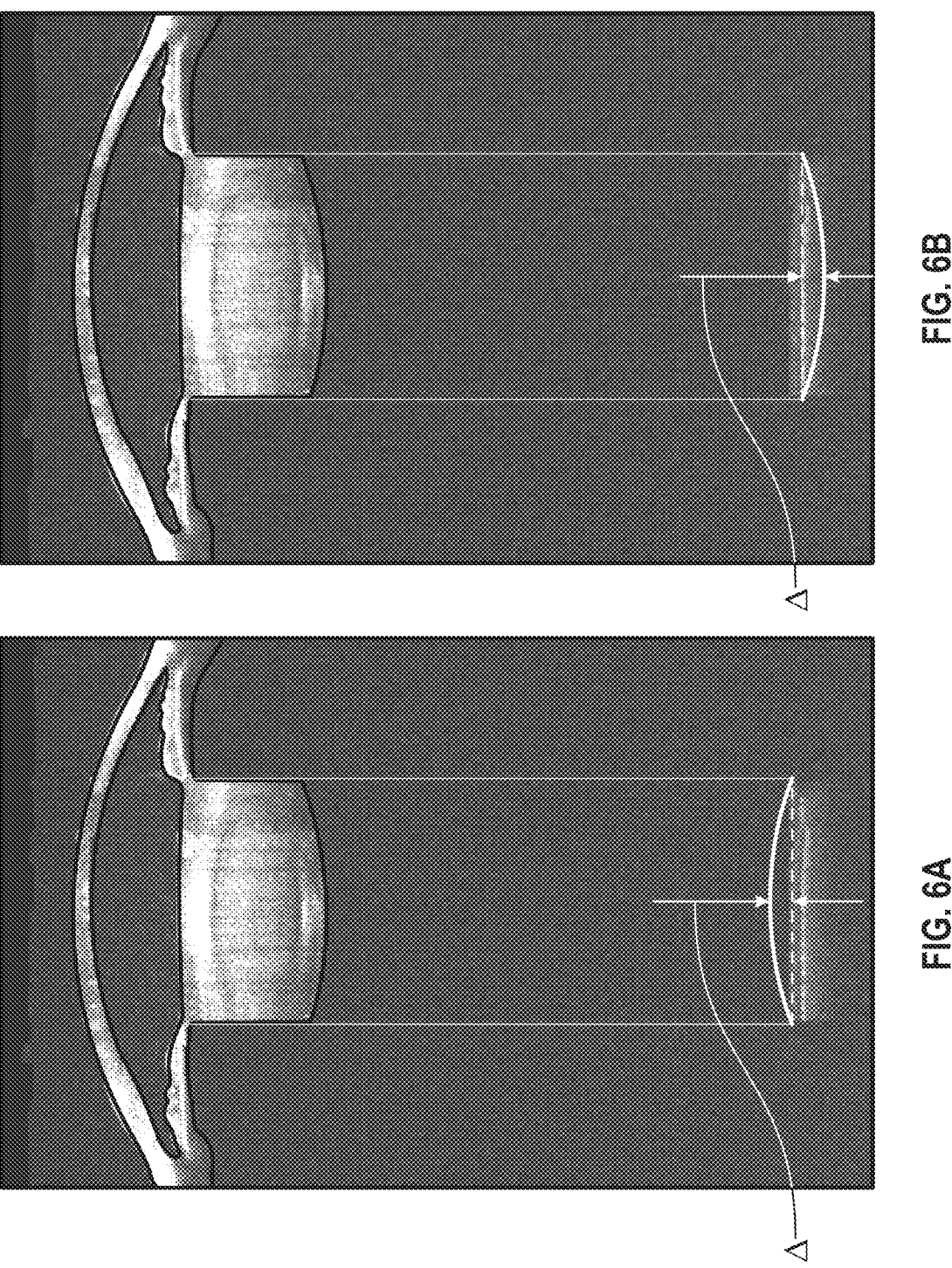
FIGS. 6A and 6B illustrates apparent image of the retina obtained for myopic and hyperopic eyes, in accordance with certain embodiments.

FIG. 6A illustrates that the line representing light reflected from the retina will bow upwardly (toward the OCT scanner) when imaging a myopic eye. FIG. 6B illustrates that the line representing light reflected from the retina will bow downwardly (away from the OCT scanner) when imaging a hyperopic eye.

Figure 7:
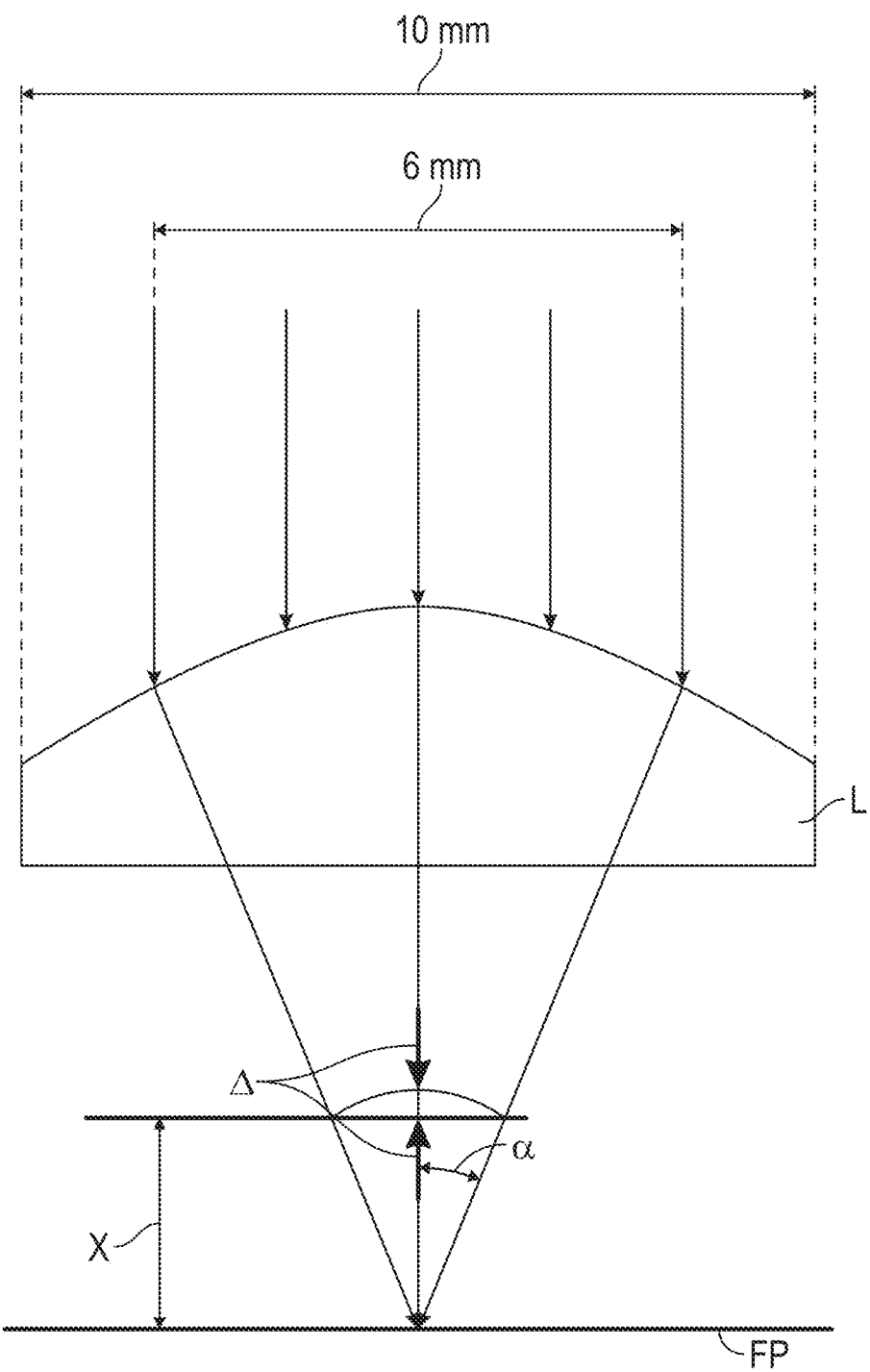
FIG. 7 is a diagram illustrating an approach for relating sag of the apparent image of the retina representing a plane to distance of the plane from a focal plane of the lens, in accordance with certain embodiments.

FIG. 7 illustrates the calculation of the sag Δ using an aspheric lens L and an OCT scanner. Δ refers to the sag of the phase front at a certain X distance from the focal plane. The OCT scanner has an OCT scan length of 6 mm (the limitation of the OCT used) and scanned horizontally across an AL108 Edmund Optics Aspheric lens having a numerical aperture (NA) of 0.55 and a 10 mm input diameter. For a 6 mm horizontal scan length the NA of the marginal OCT rays is NA=0.55*0.6=0.33. The angle of incidence a for the marginal rays is α=arc sin NA=arc sin 0.33=19.27°.

The sag Δ can be calculated as Δ=X*[(1/cos 19.27°)−1] =X*0.0594. Another way to express Δ is: Δ=59.4 μm per mm from the focal plane FP.

Figures 8A, 8B:
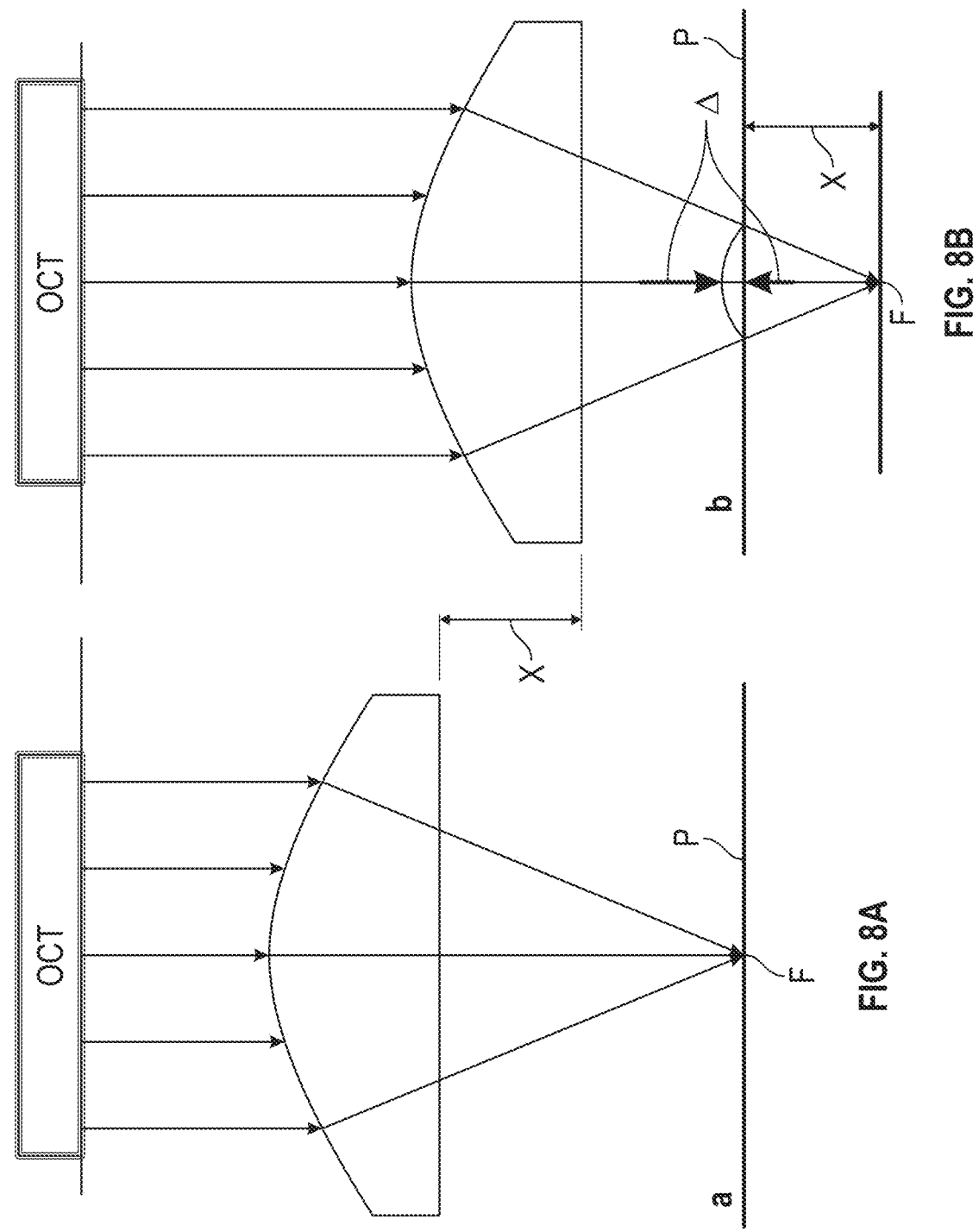
FIGS. 8A and 8B are diagrams illustrating a system for testing a relationship between the sag of the apparent image of the retina representing a plane to a distance of the plane from the focal pane of a lens, in accordance with certain embodiments.

Referring to FIGS. 8A and 8B, the value of the sag Δ was measured for multiple values of X using an anterior chamber OCT, namely an Optoview iVue OCT using the anterior chamber scanning scheme. In the experimental setup, X was changed by moving the lens L relative to the reflective plane surface P. The value of X corresponds to the distance of the lens L from a position in which the focal point of the lens L is at the reflective plane surface P. Because the OCT-to-plane P distance was unchanged, movement of the lens up and down relative to the reflective plane surface P does not move the center point of the bow like image of reflective plane surface P up or down. Instead, only the curvature of the bow-like image changes.

Figure 9:
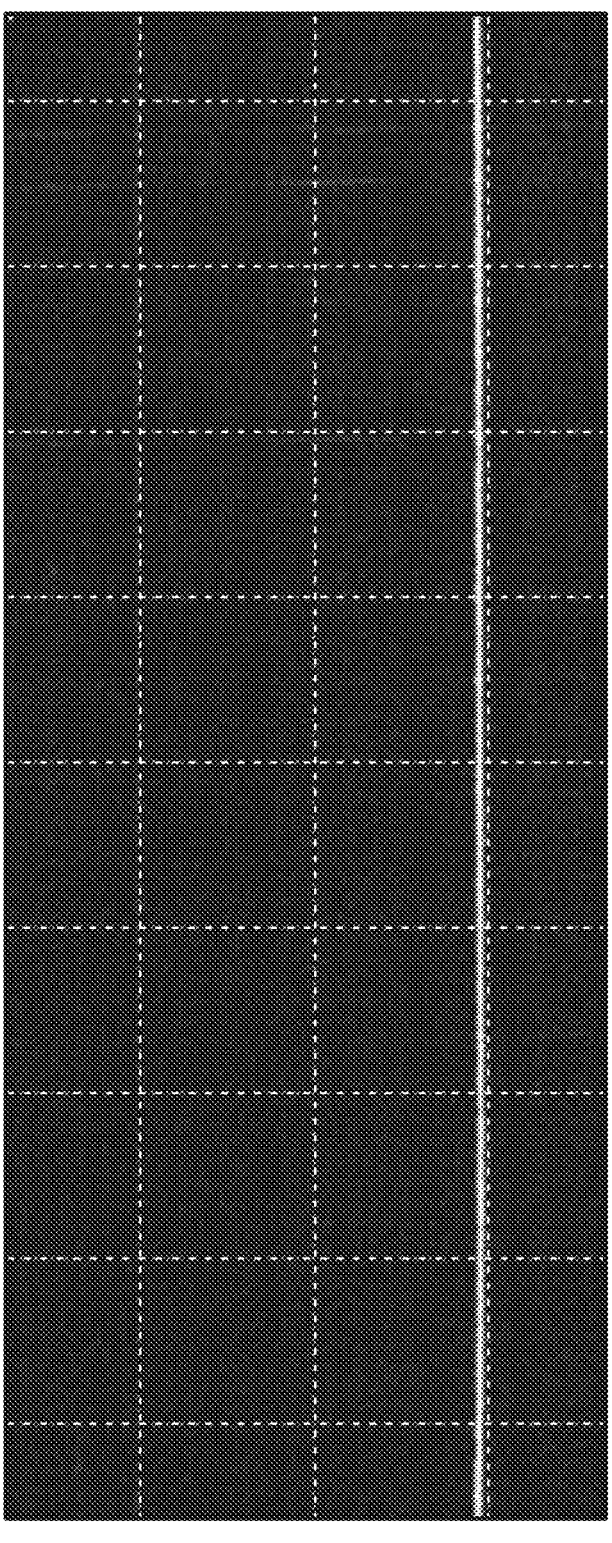
FIG. 9 is an OCT image of a reflecting surface P imaged with the OCT when the aspheric lens was not in the optical path in which the image of the reflecting surface P is a straight line proving that the rays of the scanned OCT beam are parallel to each other and the reflecting surface P is perpendicular the OCT rays.

FIG. 9 is an OCT image of plane P captured without the aspheric lens in the OCT beam. The reflecting surface P was a flat, polished stainless-steal surface. The straight line proves that the OCT scanner was optically correctly adjusted. i.e. the incident OCT rays both (a) are parallel and (b) are perpendicular to the stainless-steel surface.

Figure 10:
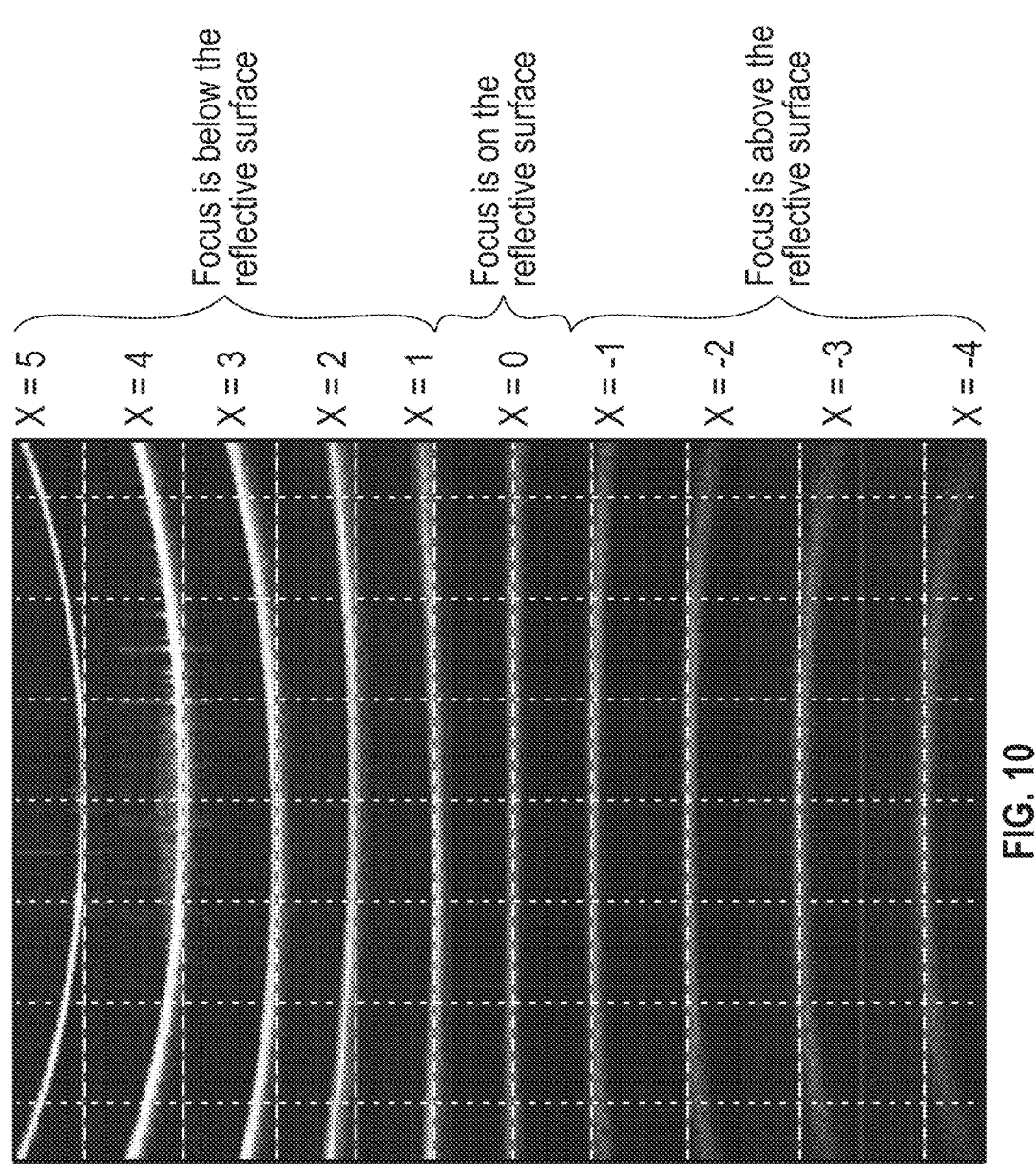
FIG. 10 is a set of OCT images of the apparent reflective surface P obtained for different vertical positions of the lens, in accordance with certain embodiments.

FIG. 10 illustrates OCT images taken with the aspheric lens in the OCT beam at various distances X relative to the initial position of FIG. 8A. For positive values of X, the focal point of the lens L is below the reflective plane surface P. For negative values of X, the focal point of the lens L is above the reflective plane surface P. X=0 corresponds to the focal point of the lens being at reflective plane surface P and therefore the image for X=0 is a straight line.

Figure 11:
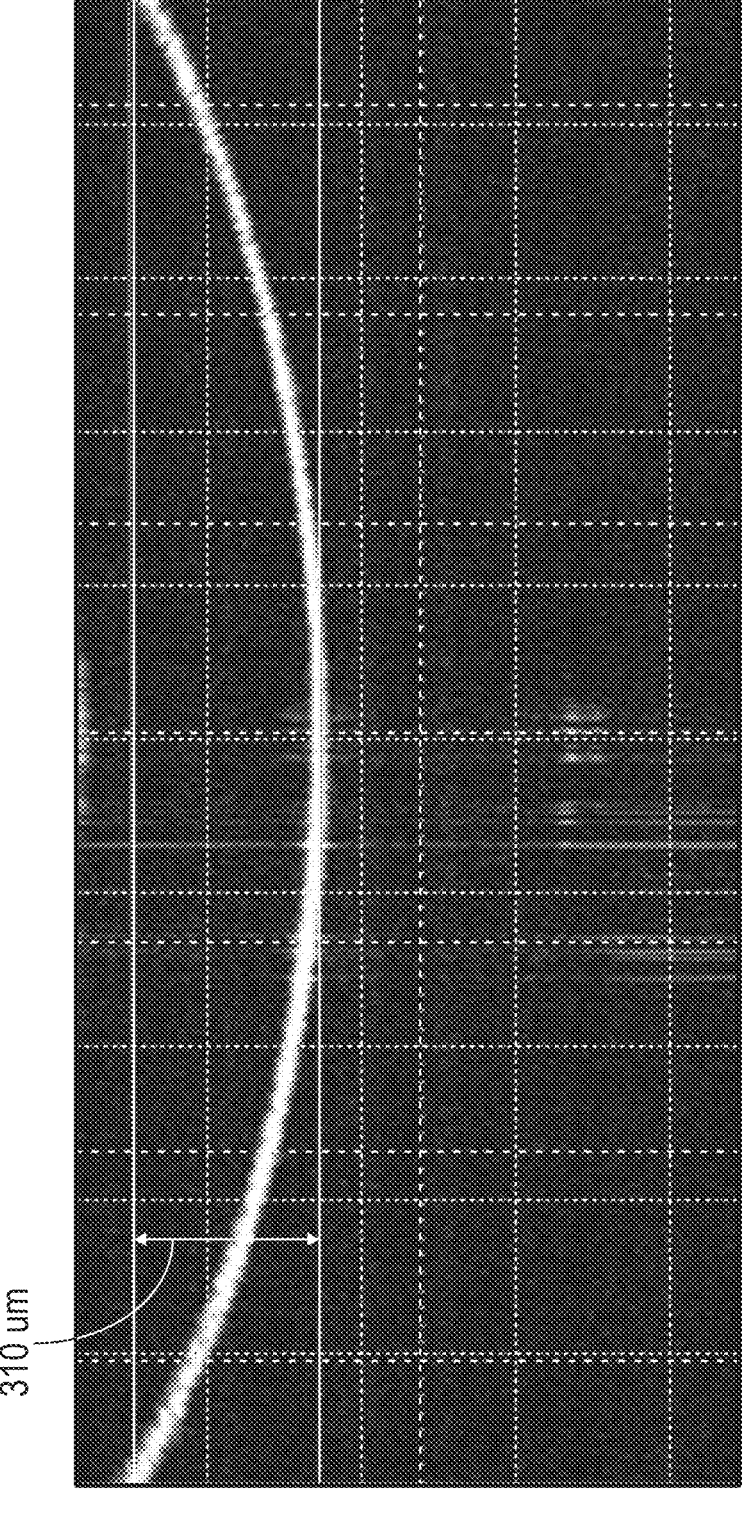
FIG. 11 is an OCT image showing the sag of the apparent image of the reflective surface P, in accordance with certain embodiments.

FIG. 11 illustrates an OCT image obtained for X=5 mm. The predicted sag Δ can be calculated as Δ=5 mm*59.4 μm/mm=297 μm. The measured sag Δ from the OCT image was 310 µm, which gives a measurement accuracy of 310/297=1.044, or 4.4%. This accuracy is acceptable in view of the available accuracy of measurement of the X shift of the aspheric lens.

Figures 12A, 12B:
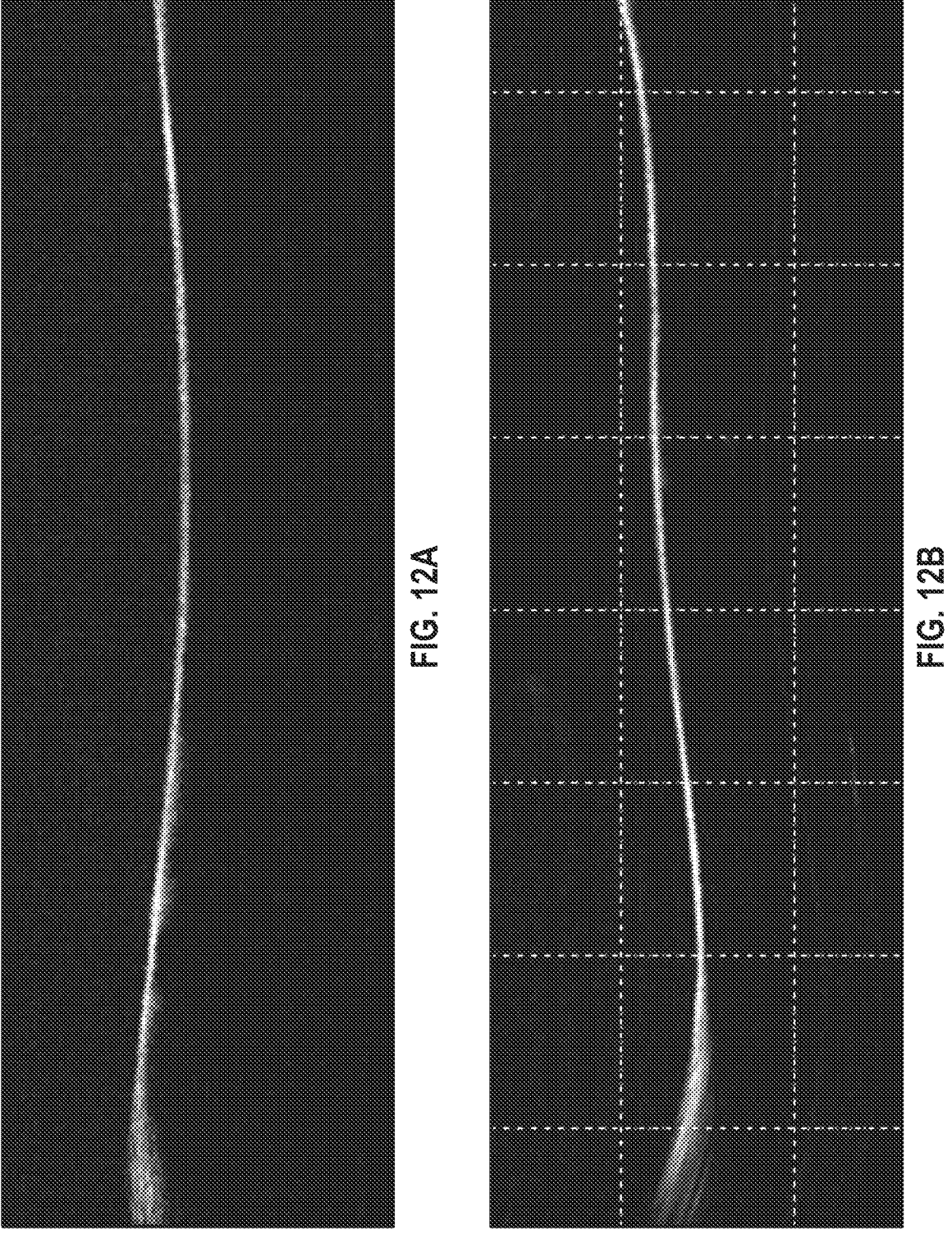
FIGS. 12A and 12B illustrate apparent images of the reflective surface P having the plane surface of the aspheric lens facing the incident OCT beam and the lens tilted to cause high order aberrations.

FIGS. 12A and 12B are OCT images showing the apparent OCT images of the reflective plane surface P in case of an optical arrangement having high order aberrations. High order aberration were introduced by tilting the lens L and by flipping the lens L such that the OCT beams were incident on the flat surface of the lens L (the aspheric lens L is designed for the arcuate surface to be illuminated).

Figure 13:
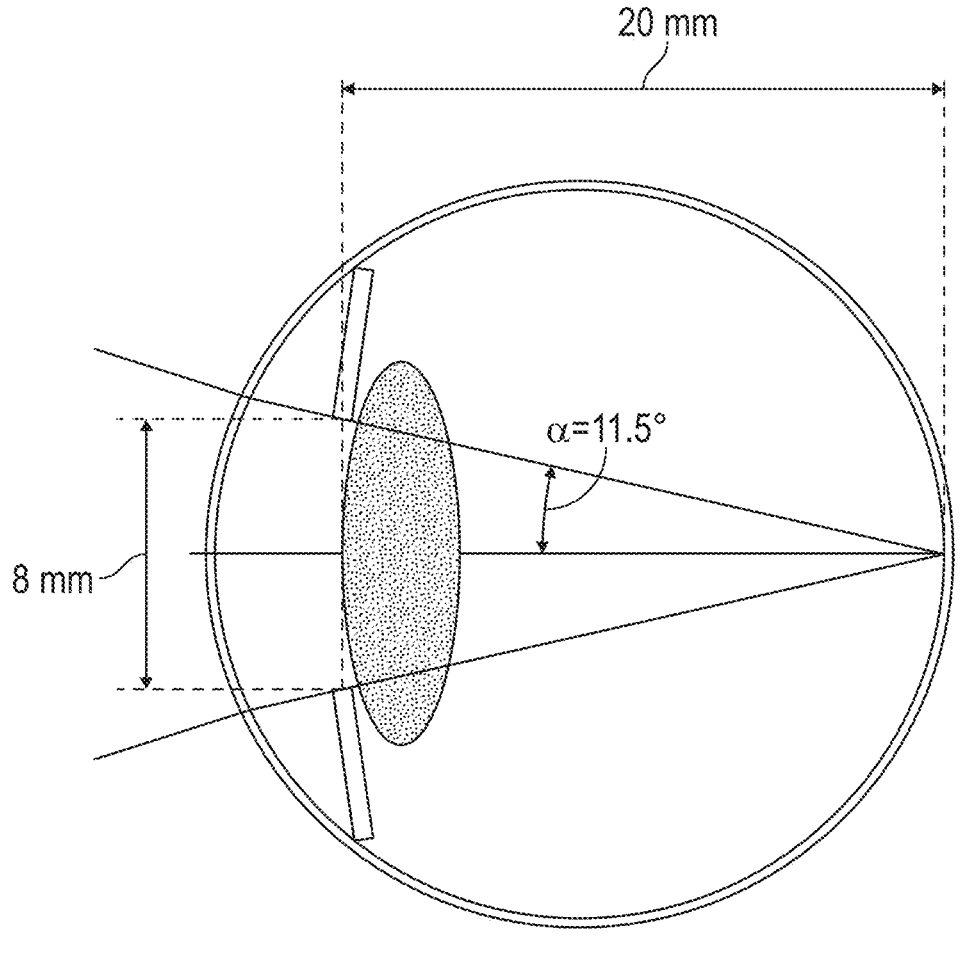
FIG. 13 is a diagram of an eye showing dimensions that may be used to calculate refractive error of the eye based on sag measured in an OCT image, in accordance with certain embodiments.

Referring to FIG. 13, the concepts outlined above may be used to measure the refractive error of an eye using an OCT image. For a typical eye, a 1 mm change in the axial length of the eye will cause a 2.82 diopter refractive error. This 2.82 number is used by different IOL (intaocular lens) calculators to select the proper IOL following cataract surgery. The following realistic example is used to estimate the resolution of an OCT based refractive error measuring device. The angle of incidence of the marginal ray for an 8 mm dilated pupil is $\alpha=\arcsin(4/20)=11.5°$. A 1 mm error in axial length will cause a sag $\Delta$ as defined earlier: $\Delta=1$ mm*[1/cos 11.5°)−1]=20.6 µm. In the vitreous, $\Delta=20.6$ µm corresponds to a distance of 1.34*20.6 µm=27.6 µm, where 1.34 is the refractive index of the vitreous. In summary, a 2.82 diopter error will cause a sag in the OCT image $\Delta=27.6$ µm (in air units). Assuming a realistic 4 µm axial resolution of the OCT the estimated refractive error resolution is therefore 2.82 diopter*4/27.6=0.41 diopter. For a 2 µm OCT resolution, which is technically also feasible, the resolution can be about 0.2 diopter. By using a proper image analysis and segmentation software, the accuracy of measurement of $\Delta$ can be an order of magnitude smaller than the depth resolution of the OCT. In this way, the measurement of the refractive error can exceed 0.2 diopter.

Recently so-called phase resolved OCT are also being developed. The software of a phase resolved OCT calculates not only the Fourier amplitude components of the interference spectrum but also the phase components. The phase resolved OCT can have much better depth resolution than 2 um and therefore phase resolved OCT based system can have much better diopter resolution.

The angle of incidence a and numerical aperture of the patient's eye is a function of measurements of the diameter of the patient's pupil and a location along the optical axis of the patient's pupil obtained using conventional techniques (including an anterior chamber OCT). The angle of incidence a is a function of a distance between the pupil and the patient's retina, which is also readily measured using an OCT scanner. Alternatively, the diameter of the pupil can be measured using a surgical microscope.

Figures 14A, 14B:
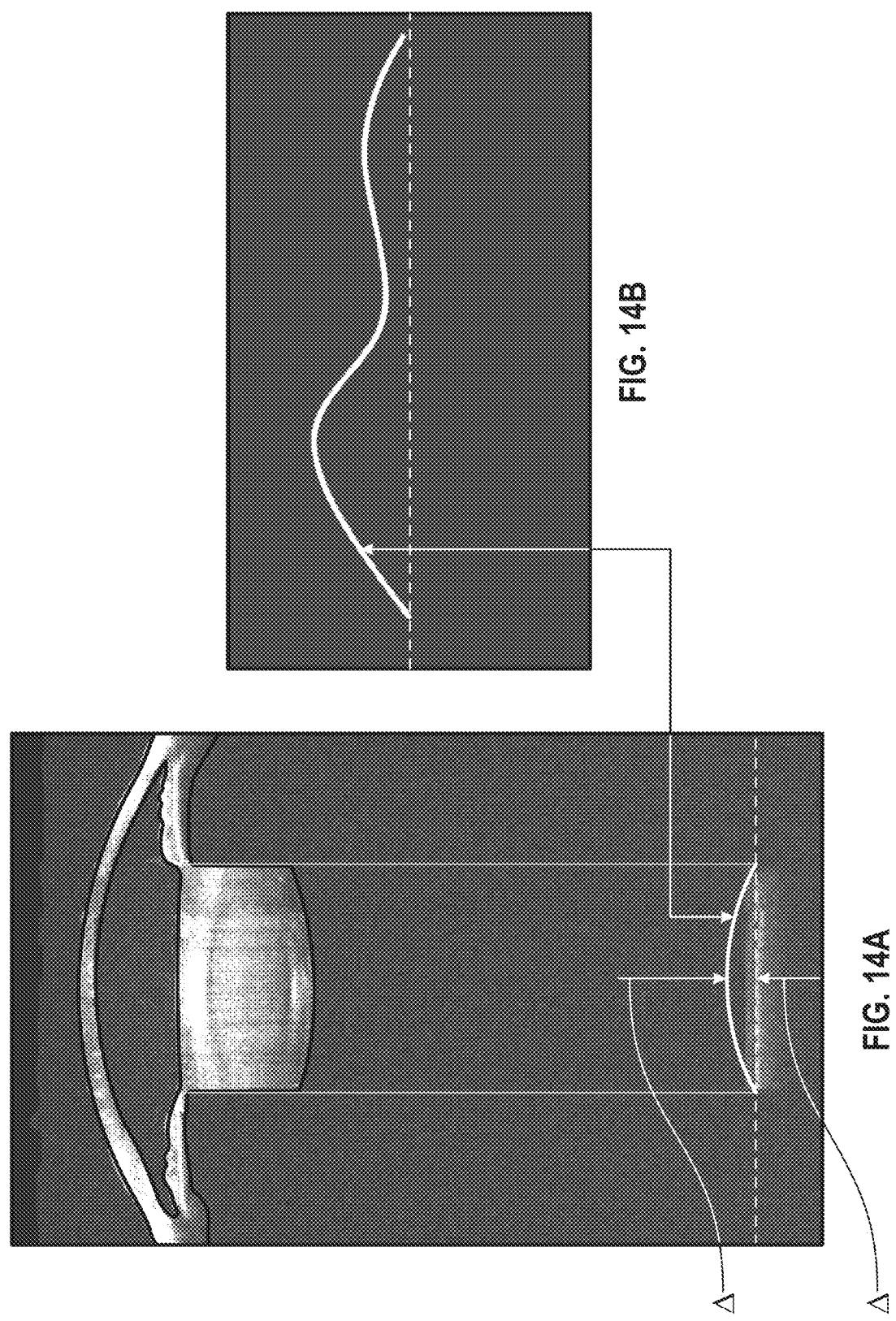
FIGS. 14A and 14B illustrate measurement of high order aberrations using an OCT image, in accordance with certain embodiments.

FIG. 14A illustrates the sag $\Delta$ for an eye having only myopic defocus error but no astigmatic or high order error resulting in a parabolic line shape. resulting from distance of the retina from the focal point of the eye. High order aberrations of an eye appear as deviation from the parabolic apparent shape of the retina as shown in FIG. 14B.

The OCT scanner can be used not only to measure the refractive spherical error but can also measure the full wavefront. For that purpose, a large plurality of A scans arranged in a raster or in a radial arrangement can be used. Accordingly, a set of OCT images is obtained, each for a different section planes of the patient's eye such that each pixel of each image represents a measurement of the eye at an X, Y, and Z coordinate within the patient's eye. The pixels representing the retina in the plurality of images (e.g., the pixels of the line representing the retina as discussed above)

may therefore be assembled to obtain a surface, i.e. a surface defined by an array of X, Y, and Z coordinates. This three-dimensional surface is in fact a wavefront elevation map that is used in wavefront science. For example, the Z value (i.e., elevation) at each (X,Y) coordinate within the three-dimensional surface represents a phase delay value of the wavefront elevation map. Where this surface bows upwardly, the patient's eye is myopic and where this surface bows downwardly the patient's eye is hyperopic with the amount of sag of the surface indicating the degree of myopia or hyperopia as described above.

A wavefront elevation map can be analyzed with well know Zernike, Fourier or Seidel method. Optical properties of the eye, e.g., modulation transfer function, point spread function, Strehl ratio, Snellen resolution, astigmatic error, coma, spherical aberration, high order aberration, lens prescription parameters, etc., can be derived from the wavefront elevation map, i.e., from the two-dimensional sag of the surface. The derivation of the optical parameters of the eye using the measured wavefront elevation map is a routine procedure for any person skilled in optics of the human eye and is not needed to describe here in detail.

An OCT scanner may be used to measure refractive error using any of the approaches herein by configuring the OCT scanner to generate strictly parallel incident beams onto the cornea. If there is some error in the parallelism of the OCT beam (caused for example by the scanning system of the OCT), then a strictly parallel test surface may be measured with the OCT. The non-parallelism of the incident OCT beam will appear on the OCT image of the test surface as a deviation from the straight line. This deviation is a calibration error and should be used during the calculation to derive the correct wavefront error of the eye.

To measure the wavefront aberration map, the reflective plane surface P (See FIGS. 8A and 8B) imaged with the OCT scanner should ideally be flat. We also have to select a flat anatomical retinal layer to measure the wavefront map of the eye. In the human eye the ideal flat anatomical layer is the Bruch's membrane Retinal Pigment Epithelium (RPE) complex. Anatomical studies showed that the existence of the foveal pit does not affect the flatness of the RPE/Bruch's complex and can be used to measure sag $\Delta$.

The following conclusions and applications follow from the approach described above:

Using the approach described herein, the refractive error of the whole eye can be obtained without the need to know the refractive indices of the cornea, the refractive index of the lens, or any topographic and geometrical data of the surfaces. All that is needed is trusting the validity of the Fermat's principle, which has been shown to be valid for the last 350 years.

The approach described herein may be performed without performing OCT-based ray tracing. This method has nothing to do with ray tracing.

The refractive error measured in diopter is approximately proportional to sag $\Delta$. Sag $\Delta$ is approximately proportional to the square of the pupil diameter.

High order aberrations appear as deviation from the parabolic sag surface of the apparent image of the retina.

An OCT can be converted to a multifunctional diagnostic tool by applying certain change to the OCT beam scanner as described below.

An anterior chamber OCT can be converted to a wavefront measuring diagnostic tool by: (a) making the incident OCT beam strictly parallel and (b) increasing the reference arm length of the OCT by the distance between the pupil and the retina, (about 20 mm), to shift the imaging zone from the anterior chamber down to the retina.

The OCT scanner implementing the approach described herein can be built into a surgical microscope used during ophthalmic surgery. In this way, the surgical microscope becomes to an intrasurgical wavefront aberrometer like the ORA (Alcon inc.) or Holos (Zeiss).

The approach for measuring the refractive error of a patient's eye as described herein may be performed using a computing device. The computing device may receive one or more OCT images from the OCT scanner or be incorporated into the OCT scanner itself. The computing device includes one or more processing devices and one or more memory devices operably connected to the one or more processing devices. The one or more memory devices store executable code that, when executed by the one or more processing devices, cause the one or more processing devices to calculate refractive error of the patient's eye as described above and any other calculations or measurements from OCT images as described above.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein but are to be accorded the full scope consistent with the language of the claims.

What is claimed is:

1. An apparatus for performing optometric measurements, comprising:
    an optical coherence tomography (OCT) imaging system configured to scan parallel beams across a patient's eye; and
    one or more processing devices;
    one or more memory devices coupled to the one or more processing devices, the one or more memory devices storing executable code that, when executed by the one or more processing devices, causes the one or more processing devices to:
        receive one or more OCT images of the patient's eye from the OCT imaging system;
        identify an apparent image of a retina of the patient's eye in the one or more OCT images, where for an eye free of optical errors, the apparent image of the retina appears as a straight line; and
        calculate a refractive error of the patient's eye from a shape of the apparent image, the shape representing a deviation of the apparent image from the straight line, and the refractive error is calculated from the deviation.

2. The apparatus of claim 1, wherein the executable code, when executed by the one or more processing devices, further causes the one or more processing devices to perform at least one of:
    if the apparent image is bowed upwardly, determine that the patient's eye is myopic; and
    if the apparent image is bowed downwardly, determine that the patient's eye is hyperopic.

3. The apparatus of claim 1, wherein the executable code, when executed by the one or more processing devices, further causes the one or more processing devices to calculate higher order aberrations of the patient's eye according to the shape of the apparent image.

4. The apparatus of claim 1 wherein the executable code, when executed by the one or more processing devices, further causes the one or more processing devices to measure the refractive error of the patient's eye by calculating a sag of the apparent image.

5. The apparatus of claim 4, wherein the executable code, when executed by the one or more processing devices, further causes the one or more processing devices to calculate the refractive error of the patient's eye by:
    obtaining an angle of incidence a corresponding to a width of a pupil of the patient's eye and a distance between the pupil and the retina; and
    calculating refractive error as a function of the sag and the angle of incidence.

6. The apparatus of claim 1, further comprising a surgical microscope, the OCT imaging system being incorporated into the surgical microscope.

7. The apparatus of claim 1, wherein the OCT imaging system is a phase sensitive OCT imaging system.

8. The apparatus of claim 1, wherein the OCT imaging system is a modified anterior chamber OCT imaging system.

9. The apparatus of claim 1, wherein the OCT imaging system is a modified anterior chamber OCT having a reference arm length selected to image the retina of the patient's eye and configured to generate parallel beams.

10. The apparatus of claim 1, wherein one of:
    (a) the one or more OCT images include a single image and the apparent image is a line in the single image representing the retina; and
    (b) the one or more OCT images include a plurality of images of a plurality of section planes of the patient's eye and the apparent image is a surface defined by an array of X, Y, and Z coordinates corresponding to pixels in the plurality of images representing the retina.

11. An apparatus for ocular imaging comprising:
    an optical coherence tomography (OCT) imaging system configured to scan parallel beams across a patient's eye;
    one or more processing devices; and
    one or more memory devices coupled to the one or more processing devices, the one or more memory devices storing executable code that, when executed by the one or more processing devices, causes the one or more processing devices to:
        receive a plurality of OCT images of the patient's eye from the OCT imaging system, each OCT image of the plurality of OCT images corresponding to light propagation time to a retina of the patient's eye as a function of a scan position of the parallel beams; and
        identify pixels in the plurality of OCT images representing a retina of the patient's eye to obtain a surface corresponding to a wavefront elevation map of the patient's eye, where for a given eye free of optical errors, the surface corresponding to the wavefront elevation map is a flat surface.

12. The apparatus of claim 11, wherein the executable code, when executed by the one or more processing devices, further causes the one or more processing devices to calculate a refractive error of the patient's eye using the wavefront elevation map.

13. A method for performing optometric measurements comprising:
    scanning, by an optical coherence tomography (OCT) imaging system, parallel beams across a patient's eye to obtain a plurality of OCT images for a plurality of section planes of the patient's eye where each OCT image of the plurality of OCT images represents light propagation time to a retina of the patient's eye as a function of a scan position of the parallel beams;

identifying pixels representing a retina of the patient's eye in the plurality of OCT images to obtain a wavefront elevation map, where for a given eye free of optical errors, the wavefront elevation map is a flat plane; and calculating a refractive error of the patient's eye using the wavefront elevation map, the calculating based on a deviation of the wavefront elevation map from the flat plane.

14. The method of claim 13, further comprising:

determining (a) that the wavefront elevation map is bowed upwardly; and in response to (a), determining that the patient's eye is myopic.

15. The method of claim 13, further comprising:

determining (a) that the wavefront elevation map is bowed downwardly; and in response to (a), determining that the patient's eye is hyperopic.

16. The method of claim 13, further comprising calculating higher order aberrations of the patient's eye according to a shape of the wavefront elevation map.

17. The method of claim 13, further comprising calculating the refractive error by calculating a sag of the wavefront elevation map.

18. The method of claim 17, further comprising:

obtaining an angle of incidence a determined by a width of a pupil of the patient's eye and a distance between the pupil and a retina of the patient's eye; and calculating the refractive error as a function of the sag and the angle of incidence a.

19. The method of claim 13, further comprising calculating refractive error of the patient's eye according to a shape of the wavefront elevation map while performing ophthalmic surgery using a surgical microscope, the OCT imaging system being incorporated into the surgical microscope.

20. The method of claim 13, wherein the OCT imaging system is a modified anterior chamber OCT imaging system.

* * * * *